US011364504B2

United States Patent
Connolly et al.

(10) Patent No.: US 11,364,504 B2
(45) Date of Patent: Jun. 21, 2022

(54) MULTIPLE ROTOR DISPOSABLE CARTRIDGE FOR PORTABLE DIAGNOSTIC ASSAY SYSTEM

(71) Applicant: Integrated Nano-Technologies, Inc., Henrietta, NY (US)

(72) Inventors: Dennis M. Connolly, Rochester, NY (US); Richard S. Murante, Rochester, NY (US); Nathaniel E. Wescott, West Henrietta, NY (US)

(73) Assignee: Integrated Nano-Technologies, Inc., Henrietta, NY (US)

( * ) Notice: Subject to any disclaimer, the term of this patent is extended or adjusted under 35 U.S.C. 154(b) by 234 days.

(21) Appl. No.: 16/311,738

(22) PCT Filed: Jun. 20, 2017

(86) PCT No.: PCT/US2017/038237
§ 371 (c)(1),
(2) Date: Dec. 20, 2018

(87) PCT Pub. No.: WO2017/223027
PCT Pub. Date: Dec. 28, 2017

(65) Prior Publication Data
US 2019/0210030 A1      Jul. 11, 2019

Related U.S. Application Data

(60) Provisional application No. 62/352,170, filed on Jun. 20, 2016.

(51) Int. Cl.
*B01L 7/00*    (2006.01)
*G01N 35/10*   (2006.01)
*C12Q 1/68*    (2018.01)

(52) U.S. Cl.
CPC .......... *B01L 7/52* (2013.01); *C12Q 1/68* (2013.01); *G01N 35/1095* (2013.01);
(Continued)

(58) Field of Classification Search
CPC .......... B01L 7/52; B01L 2200/025; B01L 2200/141; B01L 2300/0841;
(Continued)

(56) References Cited

U.S. PATENT DOCUMENTS 3,712,754 A * 1/1973 Brouwer .................. G01N 1/18
                                                              415/90
4,068,528 A * 1/1978 Gundelfinger ......... G01N 30/20
                                                              73/864.84
(Continued)

FOREIGN PATENT DOCUMENTS

DE     10222334 A1 * 12/2003    ............ G01N 30/20
JP     2008-061649 A    3/2008

OTHER PUBLICATIONS

PCT/US2017/038237; filed Jun. 20, 2017; International Search Report and Written Opinion of the International Searching Authority; dated Sep. 29, 2017.
(Continued)

Primary Examiner — Samuel P Siefke
Assistant Examiner — Tingchen Shi
(74) Attorney, Agent, or Firm — Barclay Damon LLP (57) ABSTRACT

A disposable cartridge comprises a cartridge body defining at least one syringe barrel having an barrel port configured to inject and aspirate assay fluids by displacement of a barrel plunger and at least one reaction chamber configured to receive and perform diagnostic testing on the assay fluids. The disposable cartridge also includes at least two rotors mounted for rotation to the cartridge body, each of the rotors defining a plurality of ports in fluid communication with at
(Continued)

least one of the assay chambers of a respective one of the rotors. The rotors are selectively rotated such that a port of one rotor aligns with a port of the other rotor. At least one of the rotors is disposed in fluid communication with the syringe port of the syringe barrel such that assay fluids may flows from at least one of the assay chambers through the ports of the rotors by displacement of the barrel plunger.

10 Claims, 9 Drawing Sheets

(52) U.S. Cl.
CPC ... *B01L 2200/025* (2013.01); *B01L 2200/141* (2013.01); *B01L 2300/0841* (2013.01); *B01L 2400/049* (2013.01); *B01L 2400/0478* (2013.01)

(58) Field of Classification Search
CPC ....... B01L 2400/0478; B01L 2400/049; B01L 2400/04; B01L 2200/16; B01L 2400/0622; B01L 2400/0644; B01L 3/0293; B01L 3/527; B01L 3/567; B01L 2200/0631; B01L 2300/0681; B01L 3/502; C12Q 1/68; C12Q 1/02; C12Q 1/6806; C12Q 1/6825; C12Q 2531/113; C12Q 2563/107; C12Q 2563/143; C12Q 2565/629; G01N 35/1095; G01N 35/1097; G01N 1/286; G01N 2001/2866; F16K 11/085; Y10T 137/0318; Y10T 137/8593; Y10T 137/86863; C12M 47/06; C12N 1/066; C12N 15/10; C12N 15/1013

See application file for complete search history.

(56) References Cited

U.S. PATENT DOCUMENTS

| | | | |
|---|---|---|---|
| 4,298,571 A | 11/1981 | Difulvio et al. | |
| 5,105,853 A * | 4/1992 | Lie | F16K 11/0525 251/367 |
| 6,027,691 A | 2/2000 | Watts et al. | |
| 8,716,006 B2 * | 5/2014 | Kilcoin | F16K 11/085 435/287.2 |
| 2003/0196713 A1 * | 10/2003 | Ma | F16K 11/076 137/625.47 |
| 2010/0252116 A1 | 10/2010 | Kilcoin et al. | |
| 2014/0004505 A1 * | 1/2014 | Su | G01N 33/5304 435/7.37 |

OTHER PUBLICATIONS

PCT/US2017/038237; filed Jun. 20, 2017; International Preliminary Report on Patentability; dated Dec. 25, 2018; 7 pages.

\* cited by examiner

MULTIPLE ROTOR DISPOSABLE CARTRIDGE FOR PORTABLE DIAGNOSTIC ASSAY SYSTEM

CROSS-REFERENCE TO RELATED APPLICATIONS

This application is a Non-Provisional Utility patent application which claims priority to U.S. Provisional Patent Application Ser. No. 62/352,170 filed Jun. 20, 2016 entitled "Multi-Rotor Cartridge." The contents of the aforementioned applications are hereby incorporated by reference in their entirety.

This application also relates to U.S. patent application Ser. No. 15/157,584 filed May 18, 2016 entitled "Method and System for Sample Preparation" which is a continuation of U.S. Non-Provisional patent application Ser. No. 14/056,603, filed Oct. 17, 2013, now U.S. Pat. No. 9,347,086, which claims priority to U.S. Provisional Patent Application Ser. No. 61/715,003, filed Oct. 17, 2012, which is a continuation-in-part of U.S. patent application Ser. No. 12/785,864, filed May 23, 2010, now U.S. Pat. No. 8,663,918, which claims priority to U.S. Provisional Patent Application Ser. No. 61/180,494, filed May 22, 2009, and which is also a continuation-in-part of U.S. patent application Ser. No. 12/754,205, filed Apr. 5, 2010, now U.S. Pat. No. 8,716,006, which claims priority to U.S. Provisional Patent Application Ser. No. 61/166,519, filed Apr. 3, 2009. The contents of the aforementioned applications are hereby incorporated by reference in their entirety.

TECHNICAL FIELD

This invention relates to a disposable cartridge for use in combination with a diagnostic assay system which performs RNA polymerase-DNA analysis of a biological sample. The assay system drives a rotor about a rotational axis as a syringe plunger injects and withdraws sample fluids into and out of the disposable cartridge. Embodiments of a multiple rotor disposable cartridge are disclosed including variations which facilitate flow, repeatability, reliability, admixture, and preparation of the assay fluids.

BACKGROUND

There is continuing interest to improve testing methodologies, facilitate collection and decrease the time associated with clinical laboratories. Particular testing requires that a sample be disrupted to extract nucleic acid molecules such as DNA or RNA.

The number of diagnostic tests performed annually has increased exponentially in the past decade. The use of molecular diagnostics and gene sequencing in research and medical diagnostics is also rapidly growing. For example, DNA testing has also exploded in view of the growing interest in establishing and tracking the medical history and/or ancestry of a family. Many, if not all of these assays, could benefit from a rapid sample preparation process that is easy to use, requires no operator intervention, is cost effective and is sensitive to a small sample size.

Sample collection and preparation is a major cost component of conducting real-time Polymerase Chain Reaction (PCR), gene sequencing and hybridization testing. In addition to cost, delays can lead to the spread of infectious diseases, where time is a critical component to its containment/abatement. In addition to delaying the test results, such activities divert much-needed skilled resources from the laboratory to the lower-skilled activities associated with proper collection, storage and delivery.

For example, a portable molecular diagnostic system could be operated by minimally trained personnel (such as described in US 2014/0099646 A1) and have value with regard to disease surveillance. However, the adoption of such portable systems can be limited/constrained by current methods of sample collection, which require trained personnel to permit safe and effective handling of blood/food/biological samples for analysis. Other limitations relate to: (i) handling the fluids injected into/withdrawn from the reaction chambers of disposable cartridges, (ii) cross-contamination of assay fluids which may influence the veracity of test results, and (iii) difficulties relating to independent assay testing of a multiple samples using a single common fluidic platform.

A need, therefore, exists for an improved disposable cartridge for use in combination with a portable molecular diagnostic/assay system which facilitates/enables the use of minimally-trained personnel, hands-off operation (once initiated), repeatable/reliable test results across multiple assay samples (e.g., blood, food, other biological samples) and an ability to cost effectively utilize and manufacture disposable cartridges for the diagnostic assay system.

SUMMARY

The present disclosure relates to a multiple-rotor disposable cartridge for a portable molecular diagnostic/assay system. The disposable cartridge comprises a cartridge body defining at least one syringe barrel having a barrel port configured to inject and aspirate assay fluids by displacement of a barrel plunger. The disposable cartridge also includes at least two rotors mounted for rotation to the cartridge body, each of the rotors defining a plurality of ports in fluid communication with at least one of the assay chambers of a respective one of the rotors. The rotors are selectively rotated such that a port of one rotor aligns with a port of the other rotor. At least one of the rotors is disposed in fluid communication with the syringe port of the syringe barrel such that assay fluids may flow from one of the assay chambers associated with one of the rotors through the rotor ports to the one of the assay chambers associated with the other of the rotors by displacement of the barrel plunger.

BRIEF DESCRIPTION OF THE DRAWINGS

The present invention is disclosed with reference to the accompanying drawings, wherein.

Corresponding reference characters indicate corresponding parts throughout the several views. The examples set out herein illustrate several embodiments of the invention but should not be construed as limiting the scope of the invention in any manner.

DETAILED DESCRIPTION

A disposable cartridge is described for use in a portable/automated assay system such as that described in commonly-owned, co-pending U.S. patent application Ser. No. 15/157,584 filed May 18, 2016 entitled "Method and System for Sample Preparation" which is hereby included by reference in its entirety. While the principal utility for the disposable cartridge includes DNA testing, the disposable cartridge may be used in be used to detect any of a variety of diseases which may be found in either a blood, food or biological detecting hepatitis, autoimmune deficiency syndrome (AIDS/HIV), diabetes, leukemia, graves, lupus, multiple myeloma, etc., just naming a small fraction of the various blood borne diseases that the portable/automated assay system may be configured to detect. Food diagnostic cartridges may be used to detect *salmonella, e-coli, staphylococcus aureus* or dysentery. Diagnostic cartridges may also be used to test samples from insects and specimen. For example, blood diagnostic cartridges may be dedicated cartridges useful for animals to detect diseases such as malaria, encephalitis and the west nile virus, to name but a few.

Figures 1, 2:
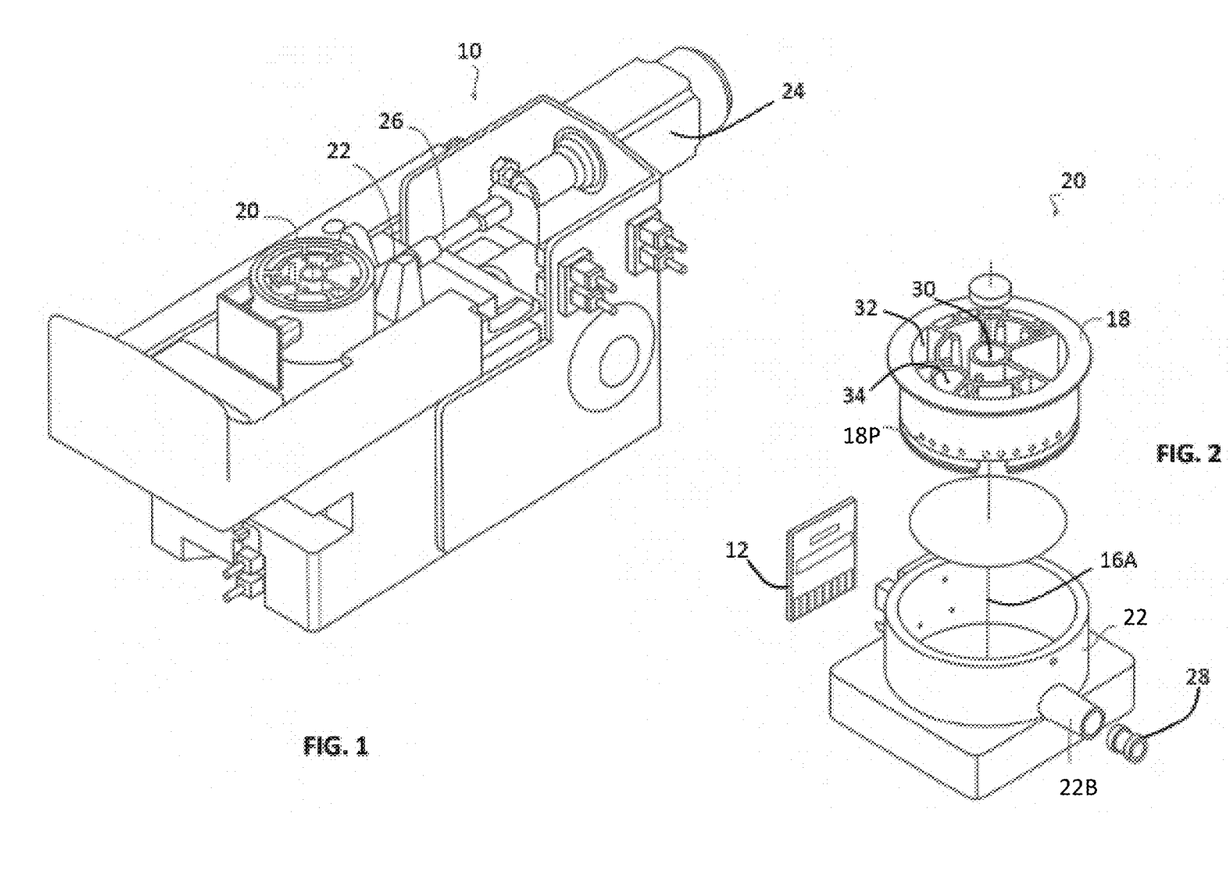
FIG. 1 is a perspective view of a portable diagnostic assay system operative to accept one of a plurality of disposable cartridges configured to test fluid samples of collected blood/food/biological samples.
FIG. 2 is an exploded perspective view of one of the disposable cartridges configured to test a blood/food/biological sample.

More specifically, and referring to FIGS. 1 and 2, a portable assay system 10 receives any one of a variety of disposable assay cartridges 20, each selectively configured for detecting a particular attribute of a fluid sample, each attribute potentially providing a marker for a blood, food or biological (animal borne) disease. The portable assay system 10 includes one or more linear and rotary actuators operative to move fluids into, and out of, various compartments or chambers of the disposable assay cartridge 20 for the purpose of identifying or detecting a fluid attribute. More specifically, a signal processor 14, i.e., a PC board, controls a rotary actuator (not shown) of the portable assay system 10 so as to align one of a variety of ports 18P, disposed about a cylindrical rotor 18, with a syringe barrel 22B of a stationary cartridge body 22. The processor 14 controls a linear actuator 24, to displace a plunger shaft 26 so as to develop pressure i.e., positive or negative (vacuum) in the syringe barrel 22. That is, the plunger shaft 26 displaces an elastomer plunger 28 within the syringe 22 to move and or admix fluids contained in one or more of the chambers 30, 32.

The disposable cartridge 20 provides an automated process for preparing the fluid sample for analysis and/or performing the fluid sample analysis. The sample preparation process allows for disruption of cells, sizing of DNA and RNA, and concentration/clean-up of the material for analysis. More specifically, the sample preparation process of the instant disclosure prepares fragments of DNA and RNA in a size range of between about 100 and 10,000 base pairs. The chambers can be used to deliver the reagents necessary for end-repair and kinase treatment. Enzymes may be stored dry and rehydrated in the disposable cartridge 20, or added to the disposable cartridge 20, just prior to use. The implementation of a rotary actuator allows for a single plunger 26, 28 to draw and dispense fluid samples without the need for a complex system of valves to open and close at various times. This greatly reduces potential for leaks and failure of the device compared to conventional systems. Finally, it will also be appreciated that the system greatly diminishes the potential for human error.

Figure 3:
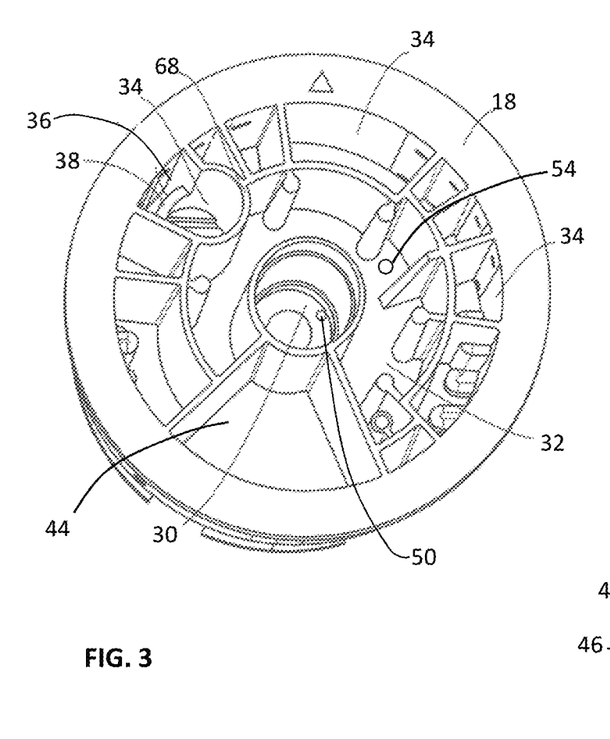
FIG. 3 is a top view of the one of the disposable cartridges illustrating a variety of assay chambers including a central assay chamber, one of which contains an assay chemical suitable to breakdown the fluid sample to detect a particular attribute of the tested fluid sample.
Figure 4:
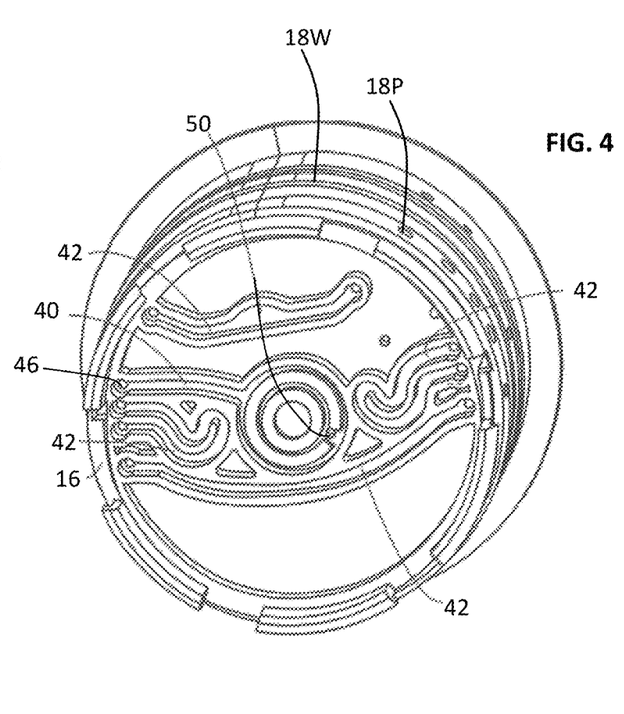
FIG. 4 is a bottom view of the disposable cartridge shown in FIG. 3 illustrating a variety of channels operative to move at least a portion of the fluid sample from one chamber to another the purpose of performing multiple operations on the fluid sample.

In FIGS. 3 and 4, the cylindrical rotor 18 includes a central chamber 30 and a plurality of assay chambers 32, 34 surrounded, and separated by, one or more radial or circumferential walls. In the described embodiment, the central chamber 30 receives the fluid sample while the surrounding chambers 32, 34 contain a premeasured assay chemical or reagent for the purpose of detecting an attribute of the fluid sample. The chemical or reagents may be initially dry and rehydrated immediately prior to conducting a test. Some of the chambers 32, 34 may be open to allow the introduction of an assay chemical while an assay procedure is underway or in-process. The chambers 30, 32, 34 are disposed in fluid communication, i.e., from one of the ports 18P to one of the chambers 30, 32, 34, by channels 40, 42 molded along a bottom panel 44, i.e., along underside surface of the rotor 18.

For example, a first port 18P, corresponding to aperture 42, may be in fluid communication with the central chamber 30, via aperture 50.

Multiple Rotor Cartridge

During development of the portable diagnostic assay system it was discovered that certain assay diagnostics required increased processing capacity, i.e., increased fluid or increased fluid flow. Furthermore, certain procedures risked the possibility for cross-contamination between reagent fluids.

Figure 5:
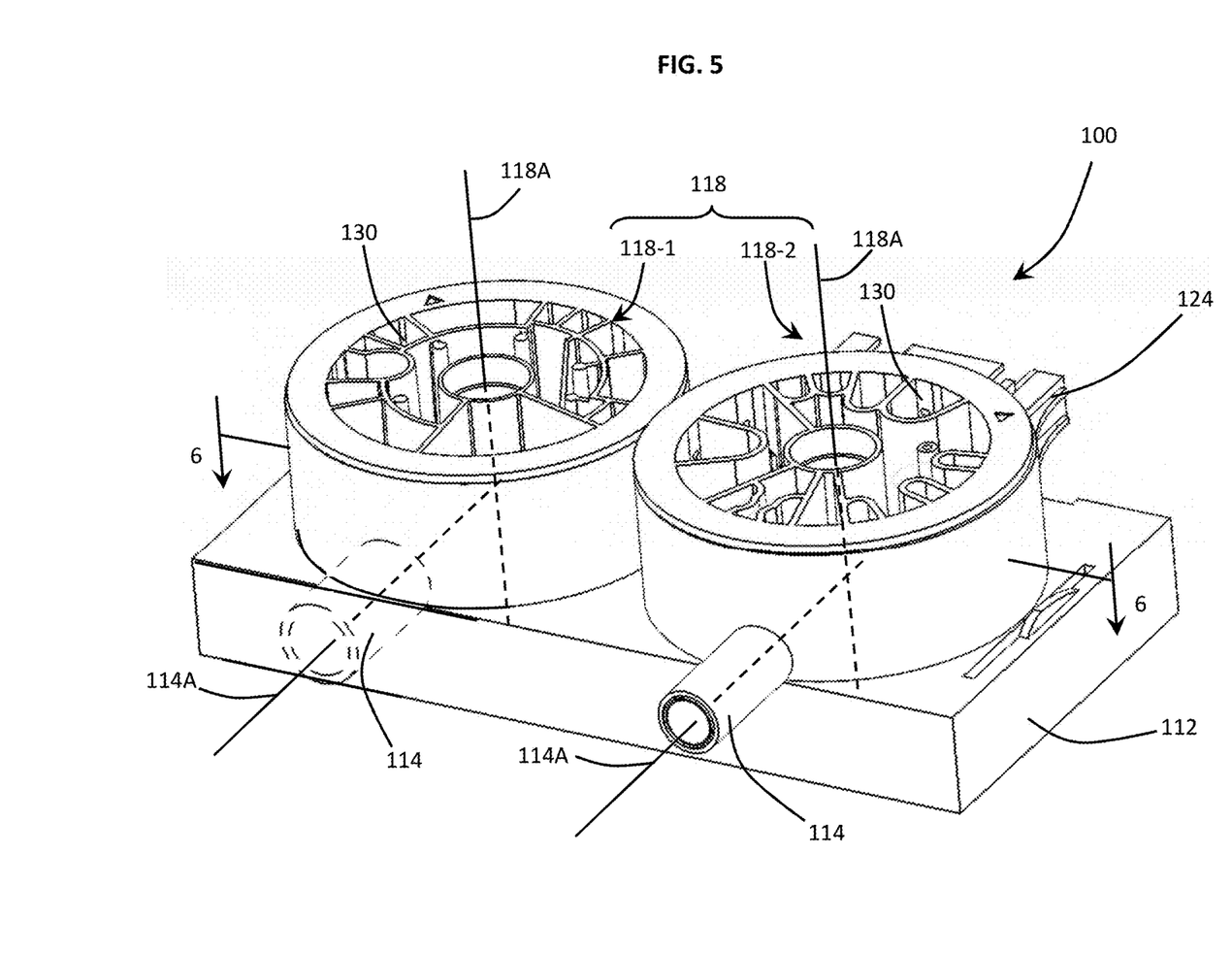
FIG. 5 depicts a perspective view of the disposable cartridge including first and second juxtaposed rotors rotationally mounted to a cartridge body including at least one syringe barrel and at least one reaction chamber.
Figure 6:
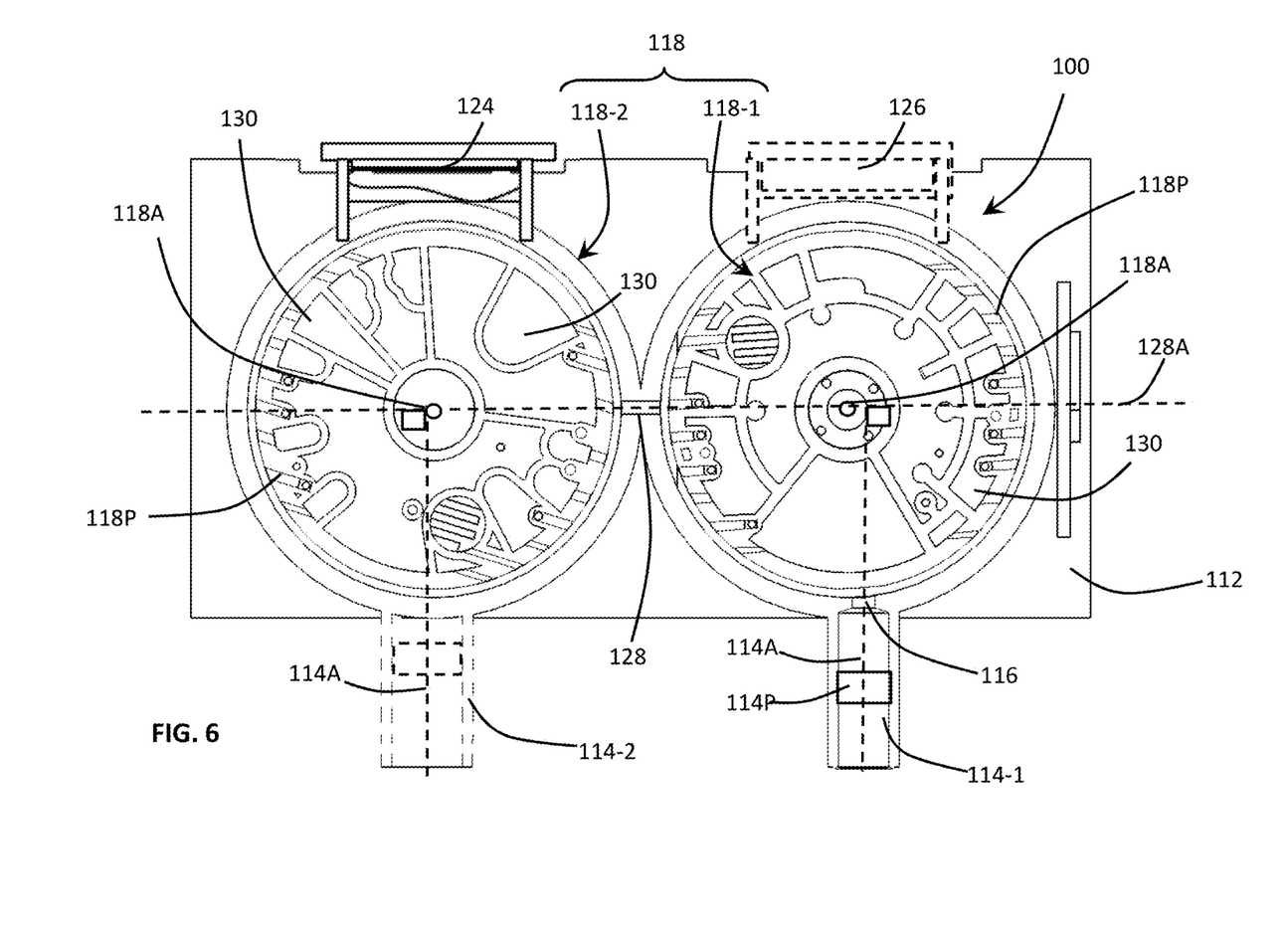
FIG. 6 is a cross-sectional view taken substantially along line 6-6 of FIG. 5 wherein a first and second rotor are disposed side-by-side and selectively rotated to align a port of the first rotor with a port of the second rotor.

In one embodiment, and referring to FIGS. 5 and 6, at least two independently driven rotors 118-1, 118-2 are rotationally mounted within a single cartridge body 112. More specifically, a disposable cartridge 100 of the disclosure includes a cartridge body 112 defining at least one syringe barrel 114 having an barrel port 116 (See FIG. 6) configured to inject and aspirate assay fluids by displacement of a barrel plunger 114P. The plunger 114P is displaced axially along an axis 114A by a linear variable displacement actuator or transducer (not shown) disposed in combination with the portable diagnostic assay system (also not shown). Similar to the single rotor cartridge 20 shown in FIG. 2, the multiple rotor disposable cartridge 100 includes a reaction chamber 124 configured to receive and perform diagnostic testing on an assay fluid.

In the described embodiment, the disposable cartridge 100 includes at least two rotors 118-1, 118-2, each comprising a plurality of assay chambers 130 rotatable about an axis 118A. In this embodiment, the rotors 118-1, 118-2 are juxtaposed and the rotational axes 118A are parallel. Each of the rotors 118-1, 118-2 is mounted for rotation to the cartridge body 112 and defines a plurality of ports 118P (see FIG. 6) disposed in fluid communication with at least one of the assay chambers 130 of a respective one of the rotors 118-1, 118-2. Each of the rotors 118-1, 118-2 is selectively rotated about the axis 118A such that a port 118P of one of the rotors 118-1, 118-2 aligns with a port 118P of the other one of the rotors 118-1, 118-2. Similar to the single cartridge rotor 18 described supra, each of the rotors 118-1, 118-2 is driven by a rotary actuator (not shown) disposed beneath the cartridge body 112. In the described embodiment, at least one of the rotors 118-1, 118-2 is disposed in fluid communication with a port 116 of the syringe barrel 114 such that assay fluids may flow from at least one of the assay chambers 130 of one of the rotors 118-1, 118-2 into the reaction chamber 124 for assay testing.

While the port 118P of one of the rotors 118-1, 118-2 may be driven to be aligned with a port 118P of the other of the rotors 118-1, 118-2, a transfer channel or port 128 may be aligned with, and disposed between, the ports 118P of both rotors 118-1, 118-2. The transfer port 128 may be tapered, i.e., conically-shaped or in the shape of an hourglass, to facilitate flow from one of the rotors 118-1, 118-2 to the other of the rotors 118-1, 118-2. In the embodiment shown in FIGS. 5 and 6, the axis 128A of the transfer port 128 is substantially orthogonal or at right angles to the axis 114A of the barrel port 114.

In the embodiment depicted, the syringe plunger 114P (see FIG. 6): (i) injects and withdraws assay fluids from the assay chambers 130 of the first rotor 118-1, and (ii) moves fluid through the ports 118P of the first and second rotors 118-1, 118-2 or, alternatively, through the transfer port 128, to cause the assay fluids to move across the rotors for processing. While, in the illustrated embodiment, a reaction chamber 124 receives assay fluids from the second rotor 118-2, a second reaction chamber or an auxiliary processing device 126 may also be in fluid communication with the first rotor 118-1. That is, after such assay fluids are transferred back from the second rotor 118-2 to the first rotor 118-1, i.e., for a second time, through the transfer channel or port 128. This flow path is described in one of the other embodiments depicted in Figs. 11a-11c to increase system processing capacity and prevent cross-contamination of reagent fluids.

Alternatively, no reaction chamber or auxiliary processing device 124, 126 is needed to benefit from the multiple rotor cartridge. For example, the assay fluid may be amplified in the multiple rotor cartridge for subsequent assay testing on a separate diagnostic device (not shown).

In another embodiment of the multiple rotor cartridge 100, the multiple rotor cartridge 100 may include both an auxiliary processing device 126 and a reaction chamber 124. In this embodiment, the auxiliary processing device 126 may be in fluid communication with either of the rotors 118-1, 118-2 to perform an interim step in the process of identifying an attribute of the assay fluid. Such auxiliary processing devices 126 may include heating and cooling elements for PCR, optical detection, electronic detectors, and/or mechanical/ultrasonic mixers. Thereafter, the assay fluid may be transferred to the reaction chamber to perform diagnostic testing on the assay fluid.

Each of the rotors 118-1, 118-2 may direct assay fluids to a reaction chamber 124 disposed adjacent one of the rotors 118-1, 118-2. Similarly, each of the rotors 118-1, 118-2 may receive injected assay fluid from one or two syringes barrels 114-1, 114-2. Therefore, the multiple rotor cartridge 100 may include two (2) or more syringe barrels 114-1, 114-2 (along with the respective plunger 114P), an auxiliary processing device 126, and a reaction chamber 124. These configurations have the benefit of providing additional processing capability within a prescribed time period.

Figure 7:
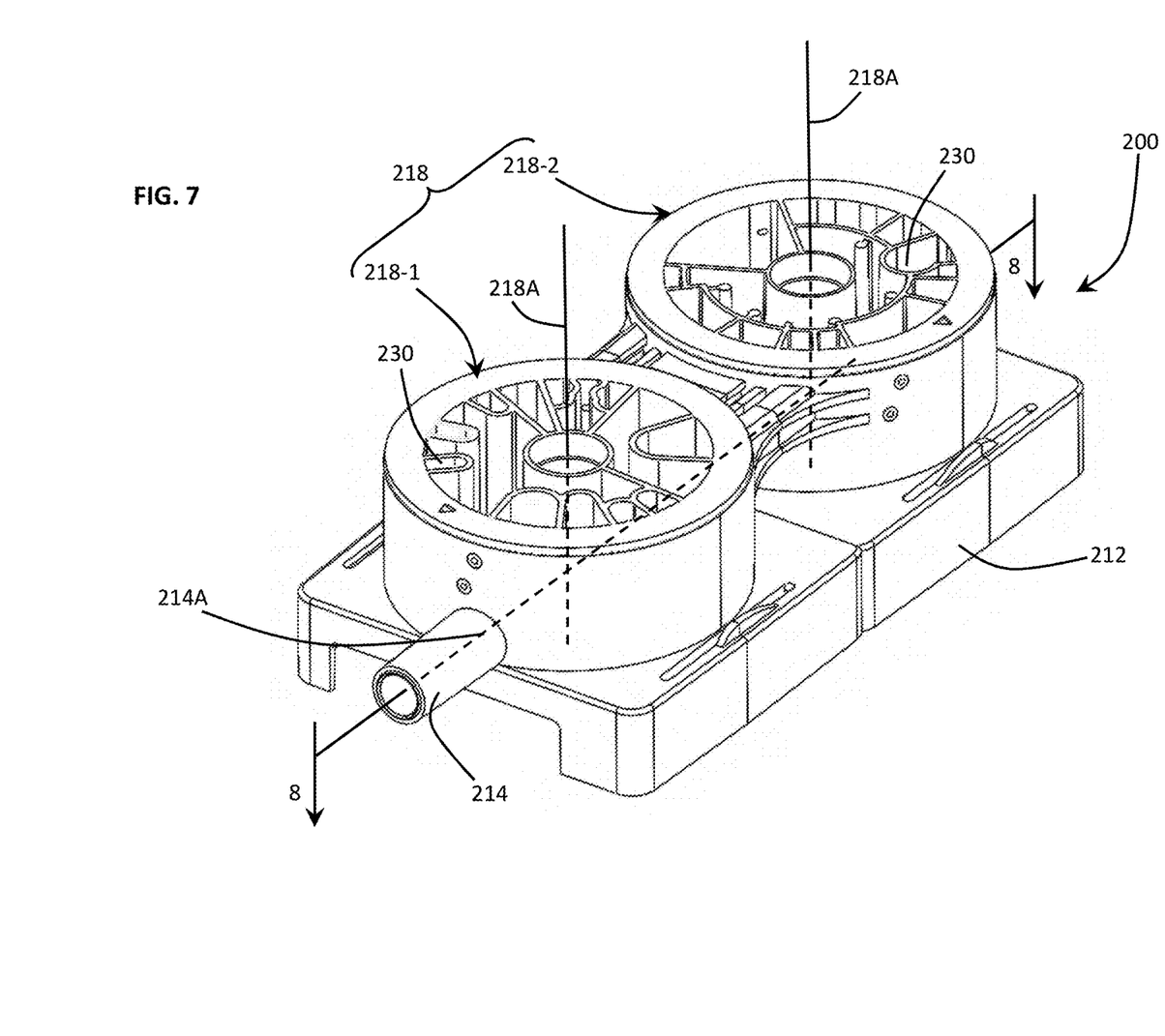
FIG. 7 is a perspective view of another embodiment of a multiple rotor disposable cartridge having tandem rotors wherein the axes thereof are parallel.

In FIG. 7, another embodiment of a multi-rotor disposable cartridge 200 is depicted wherein the rotors 218-1, 218-2 are tandemly-arranged such that at least one syringe barrel 214 faces forwardly. More specifically, the axis 214A of the syringe barrel 214-1, 214-2 intersects both of the rotors 218-1, 218-2. Stated in yet another manner, the rotor axes 218A are parallel and lie in a plane 226 which is substantially parallel to the axis 214A of the syringe barrel 214-1, 214-2. In this embodiment, assay fluids may be transferred back and forth into the tandemly-arranged second rotor 218-2 to perform many of the PCR reactions that, heretofore, were performed by a single rotor cartridge 20. Accordingly, the time required to strip and amplify the DNA while performing the PCR process steps can be increased by a factor of two (2) or four (4) depending upon the number of zones in the second rotor 218-2 dedicated to amplification of the target fluid.

Figure 8:
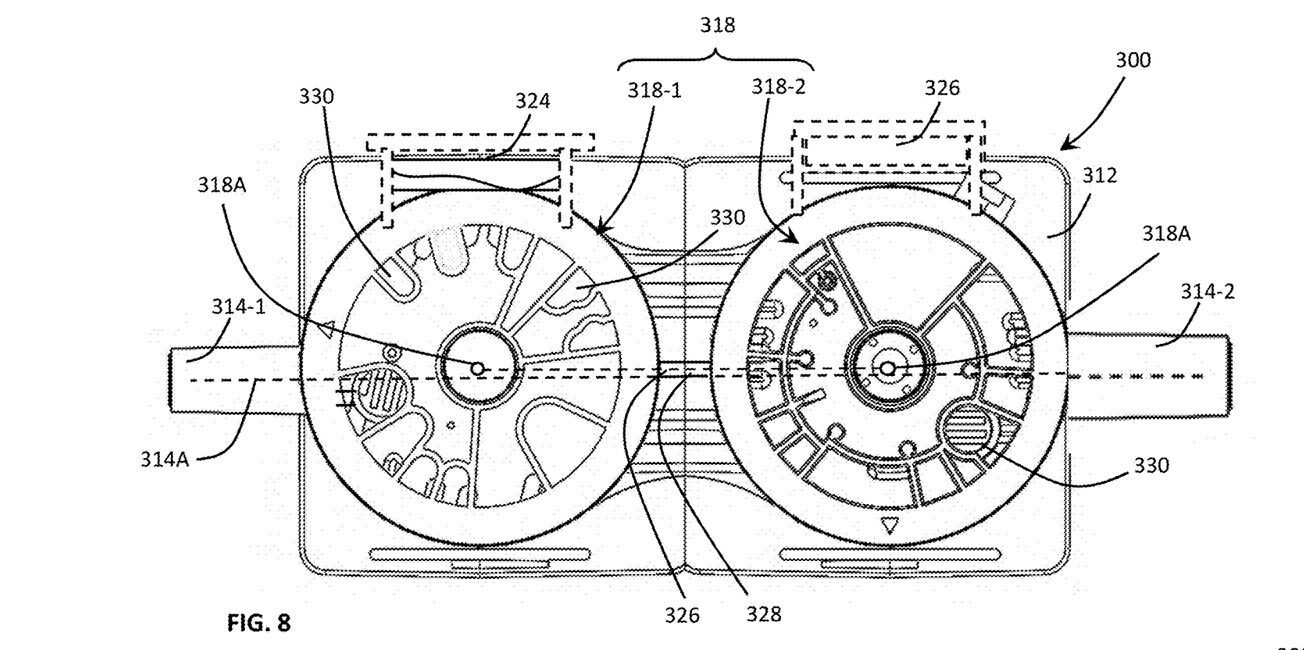
FIG. 8 is a modified cross-sectional view taken substantially along line 8-8 of FIG. 7 depicting another embodiment wherein the syringe barrels are back-to-back, i.e., one facing forwardly and the other facing rearwardly, and the axes of the rotors are parallel.
Figure 8A:
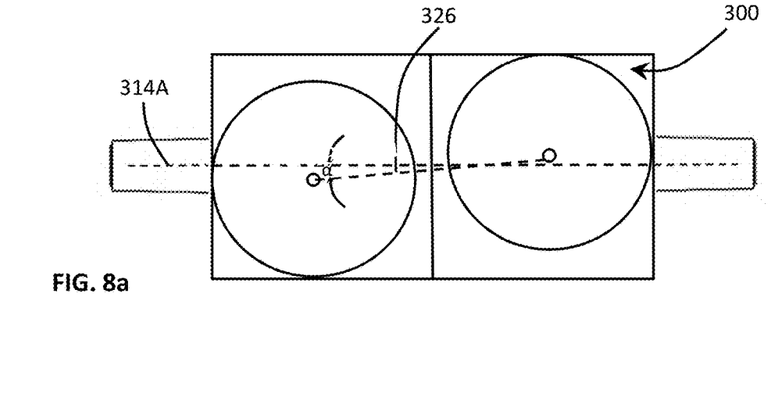
FIG. 8a depicts a schematic view of the sectional view of FIG. 8 depicting a variation of the rotor geometry effecting the relationship of the syringe axis to a plane defined by the pair of parallel rotor axes.

In FIG. 8, another embodiment of the multi-rotor disposable cartridge 300 shows the rotors 318-1, 318-2 in a back-to-back configuration such that a first syringe barrel 314-1 faces forwardly and a second syringe barrel 314-2 faces rearwardly. Once again, the axes 318A of the rotors 318-1, 318-2 are parallel and lie in a plane 326 which is substantially parallel to the axis 314A of the syringe barrel 314. In the context used herein, the term "substantially parallel" means that that the axis 314A defines an acute angle α relative to the plane 326 which is less than about twenty-degrees (20°) (see FIG. 8a) relative to the plane 326 defined by the axes 318A of the rotors 318-1, 318-2.

Figure 9:
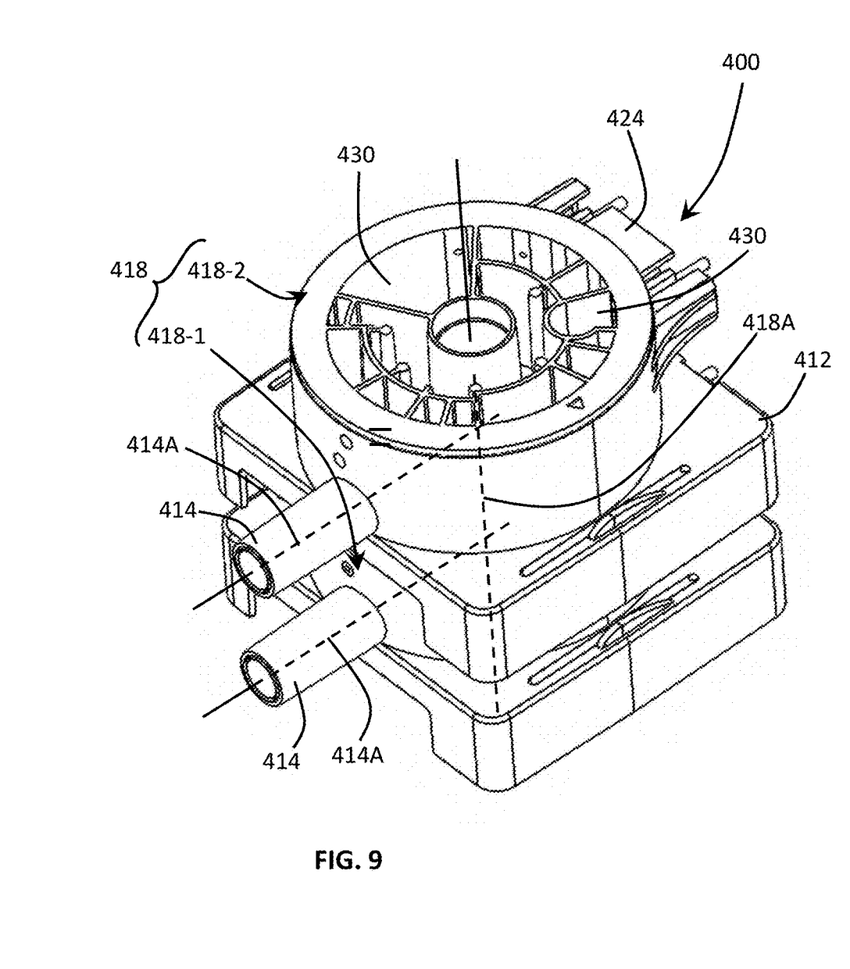
FIG. 9 depicts another embodiment of the multiple rotor disposable cartridge wherein the rotors are stacked such that the axes are coaxial.

In FIG. 9, another embodiment of the multi-rotor disposable cartridge 400 shows a second rotor 418-2 disposed over a first rotor 418-2. That is, the rotors 418-1, 418-2 are stacked such that the rotational axes 418A are coaxial and, at least partially, coincident. In this embodiment, a port (not shown) associated with the first rotor 418-1 is selectively aligned with a second port (also not shown) of the second rotor 418-2. The aligned ports are oriented vertically and substantially parallel to the coaxial rotational axes 418A of the stacked rotors 418-1, 418-2. In this embodiment, the axis 414A of the syringe barrel 414 is orthogonal relative to the rotational axes 418A of the rotors 418-1, 418-2. Furthermore, each of the rotors 418-1, 418-2 may be aligned with a syringe barrel 414. While the upper portion of the cartridge body 412 shows a reaction chamber 424 receiving assay fluids from the second rotor 418-2, it should be appreciated that either of the rotors 418-1, 418-2 may transfer assay fluids to a reaction chamber 424 of the cartridge body 412.

Figure 10:
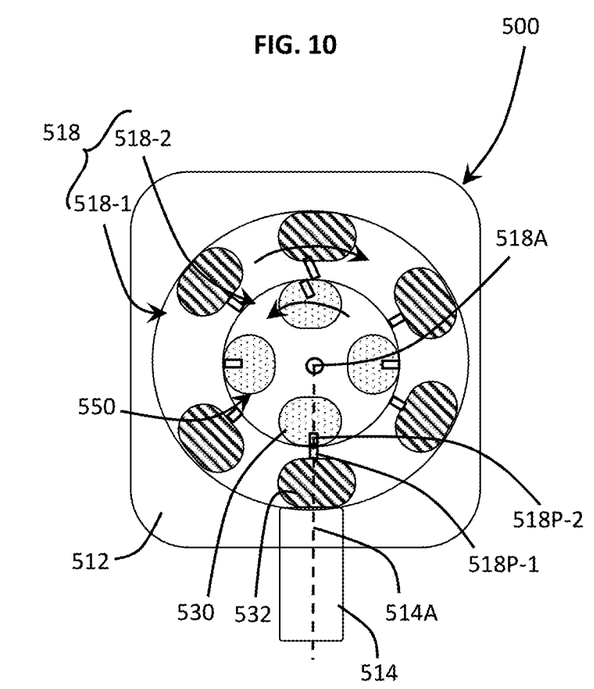
FIG. 10 depicts another embodiment of the multiple rotor disposable cartridge wherein a first rotor defines an annular-shaped ring or torus and a second rotor seats within a cavity produced by the annular-shaped ring or torus of the first rotor and wherein the first and second rotors are driven about a common axis.

In FIG. 10, another embodiment of the multiple-rotor diagnostic cartridge 500 employs a first rotor defining an annular or torus shaped portion 518-1 providing a central cavity 550 for receiving a second rotor 518-2. The first and second rotors 518-1, 518-2 may be driven in the same or opposite directions, i.e., clockwise or counter-clockwise directions, about a common axis 518A to align a radially inwardly facing port 518P-1 of the first rotor 518-1 with a radially outwardly facing port 518P-2 of the second rotor 518-2. As such assay fluids may pass back and forth between a chamber 530 associated with the first annular rotor 518-1 and a chamber 532 associated with the second cylindrical rotor 518-2. In this embodiment, the axis (not shown) of the syringe barrel (normal to the plane of the page) may be orthogonal to the plane of the annular ring or torus 518-1 such that the barrel port aligns with any of the chambers 530, 532 as they rotationally pass the vertically-oriented barrel port.

Figures 11A, 11B, 11C:
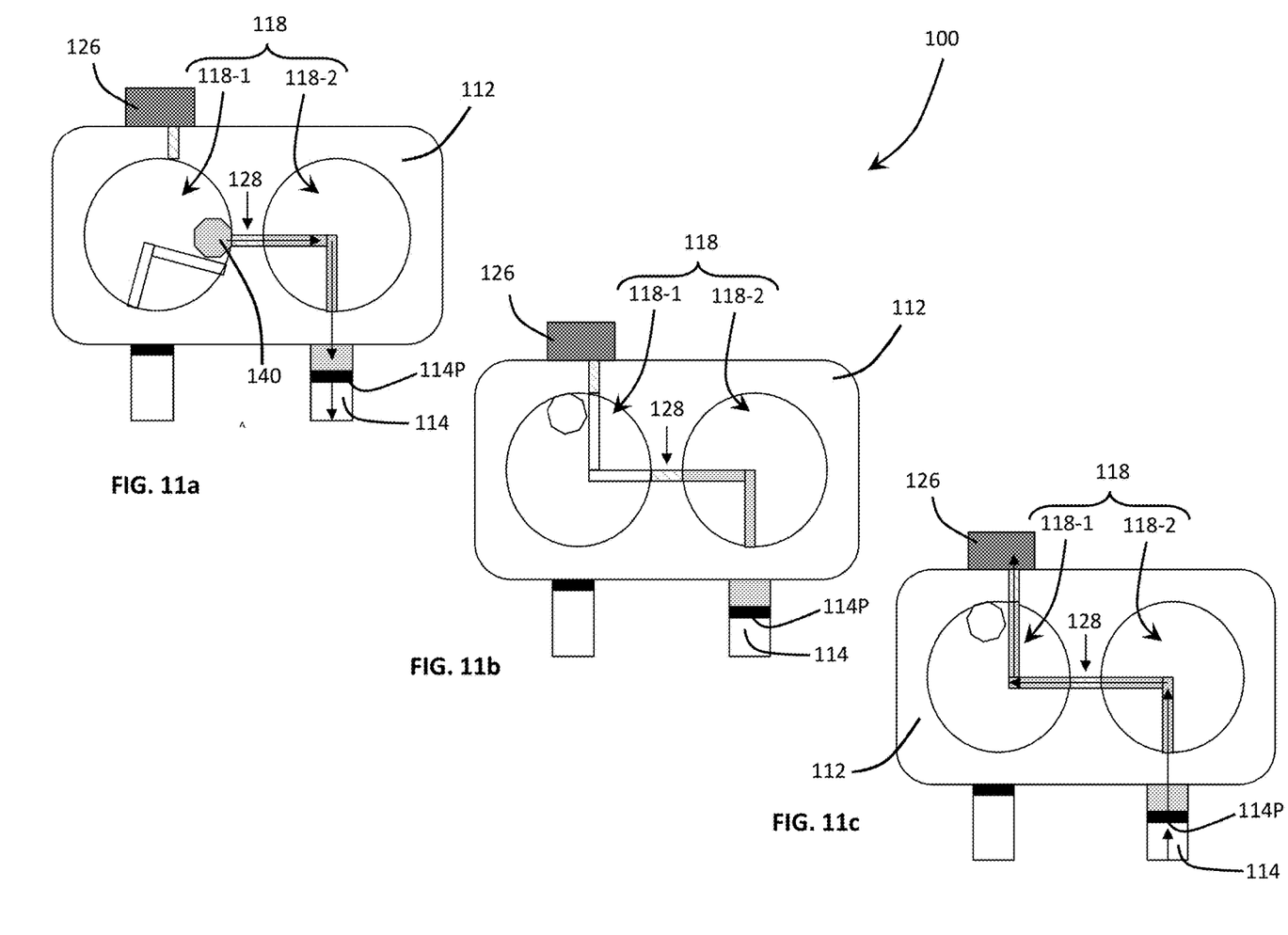
FIGS. 11a-11c are schematic views of a multiple rotor cartridge depicting a sequence of aspiration/injection steps which prevent cross-contamination of assay fluids while improving processing capacity.

FIGS. 11a-11c depict a sequence of aspiration and injection steps to prevent cross-contamination of one reagent from contacting another reagent. The sequence depicted prevents specific reagents from contacting a reagent in the first rotor 118-1 while preventing contamination of the syringe barrel 114. In FIG. 11a, the first and second rotors 118-1, 118-2 are both aligned with the transfer channel 128 such that a fluid path is produced from a reagent-filled chamber 140 to the syringe barrel 114. As such, the syringe plunger 114P may aspirate the reagent-filled chamber 140 into the syringe barrel 114.

In FIG. 11b, the first rotor 118-1 is rotated to a position which creates a flow path from the transfer channel 128 to a desired location. In this instance, the desired location is one of the auxiliary processing devices 126 to augment processing of the assay fluid, e.g., to perform an amplification step. Accordingly, the assay fluid from the reagent-filled chamber 140 is not exposed to fluids from another chamber or another port, but rather removed from the chamber 140 by moving the assay fluid into the syringe barrel 114.

In FIG. 11c, the syringe plunger 114P is displaced axially to inject the reagent into an auxiliary processing device 126. As mentioned earlier, the auxiliary processing device 126 may include may include a heating and cooling element for PCR processing, optical detection, electronic detectors, and/or mechanical/ultrasonic mixers, etc. In addition to avoiding contamination of an assay fluid, the multiple rotor cartridge greatly improves the processing capacity of the disposable cartridge 100. That is, by manipulating assay fluids in this manner, multiple process steps may be performed simultaneously greatly accelerating the processing capability of the disposable cartridge 100.

Figure 12:
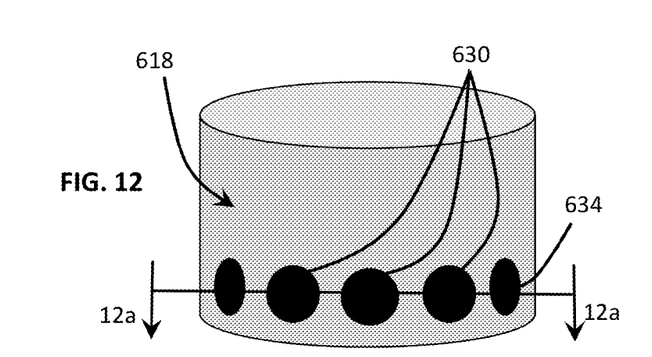
FIG. 12 is a schematic profile view of a rotor having at least one internal syringe barrel each having an internal plunger for injecting or withdrawing assay fluids from one rotor to another rotor.
Figure 12A:
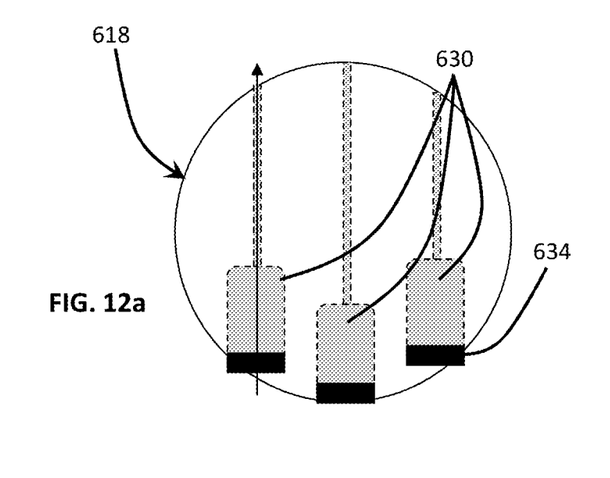
FIG. 12a is a cross-sectional view taken substantially along line 12a-12a of FIG. 12 depicting a plurality of horizontally-oriented syringe barrels for injecting and withdrawing assay fluids from the assay chambers of a rotor.
Figure 13:
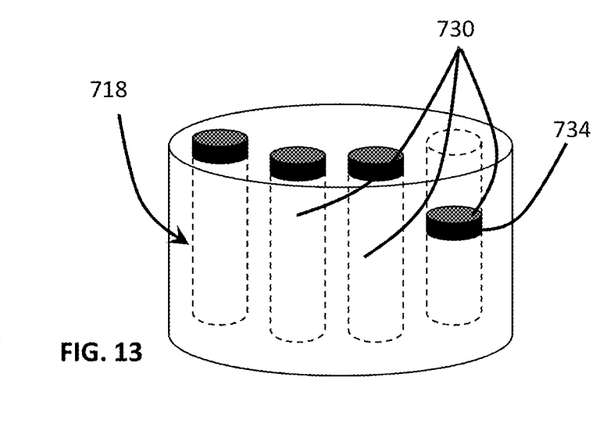
FIG. 13 is a schematic side view of a rotor having a plurality of vertically-oriented syringe barrels each having an internal plunger for injecting and withdrawing assay fluids from one rotor to another rotor.

FIGS. 12, 12a, and 13 depict hybrid rotors 618, 718 which may be used in a single or multiple rotor disposable cartridge 20, 100, 200, 300, 400 and 500. In this embodiment, the rotors 618, 718 contain a bore or cavity 630, 730 which may be used to inject or withdraw assay fluids directly into a chamber of another rotor, an auxiliary processing device, or a reaction chamber. The embodiment shown in FIGS. 12 and 12a depict a radially or horizontally oriented bore, i.e., relative to the rotational axis 618A of the rotor 618. On the other hand, the embodiment shown in FIG. 13, depicts a vertically oriented bore 730 which is parallel to the rotational axis 718A of the rotor 718. Each of the bores 630, 730 receive a plunger 634, 734 operative to pressurize the assay fluid to move assay fluids into and out of the rotors 618, 718.

Figure 14:
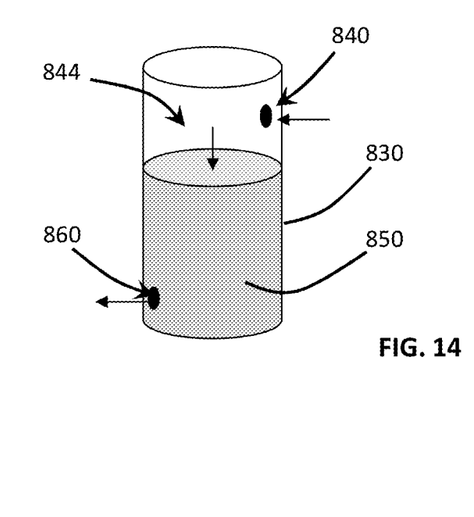
FIG. 14 depicts an enlarged isolated view of a single chamber including an inlet port disposed over an outlet port for the purpose of pressurizing an upper volume of the chamber to effect flow through the lower outlet port.

FIG. 14 is an enlarged view of a single bore, cavity or chamber 830 of a rotor. In this embodiment, the pressurized bore 830 includes an inlet port 840 providing access to a void region 844 disposed over or above the assay fluid 850 and an outlet port 860 proximal an end or bottom of the chamber 830. A fluid (e.g., air) may be pumped into the inlet port 840 to create flow through the outlet port 860. As such, a plunger or other positive pressurization device may be eliminated.

While each rotor of a multirotor cartridge is described and depicted as having a single syringe barrel, it should be appreciated that the cartridge body of each multiple rotor cartridge may having multiple syringe barrels each having a syringe plunger. As such, assay fluids from each rotor and/or each chamber may be received and or aspirated for assay testing. While each cartridge is shown to include a pair of rotors, it will be appreciated that additional rotors may be incorporated within, and mounted to, the cartridge body. For example, three rotors may be stacked along a common axis to move assay fluids across the interface of each. Similarly, three rotors may be disposed in a triangular shape along with multiple transfer ports therebetween to move assay fluids between the assay chambers of each rotor. The same three rotors may be disposed in tandem with one or more syringe barrels associated with each to inject and aspirate the assay fluids from each of the rotors.

While the invention has been described with reference to particular embodiments, it will be understood by those skilled in the art that various changes may be made and equivalents may be substituted for elements thereof without departing from the scope of the invention. In addition, many modifications may be made to adapt a particular situation or material to the teachings of the invention without departing from the scope of the invention.

Therefore, it is intended that the invention not be limited to the particular embodiments disclosed as the best mode contemplated for carrying out this invention, but that the invention will include all embodiments falling within the scope and spirit of the appended claims.

What is claimed is:

1. A disposable cartridge for use in combination with a diagnostic assay system, comprising:
    a cartridge body defining at least one syringe barrel having an barrel port operative to inject and withdraw assay fluids in response to a displacement of a syringe plunger;
    a plurality of rotors each comprising a plurality of assay chambers surrounded by a radial wall and rotatable about an axis and mounted for rotation to the cartridge body, each of the plurality of rotors defining a plurality of ports disposed about a peripheral surface and in fluid communication with at least one of the assay chambers of a respective one of the rotors, the plurality of rotors defining a first rotor and a second rotor, the ports of the first rotor capable of being rotated into alignment with the barrel port of the syringe barrel, while the ports of the second rotor are capable of being selectively rotated into alignment with at least one of the ports of the first rotor such that a port axis extends through the aligned ports;

at least one auxiliary processing device disposed in fluid communication with one of the assay chambers of the first and second rotors, the auxiliary processing device performing an interim step in a process of identifying an attribute of the assay fluid; and at least one reaction chamber disposed in fluid communication with one of the assay chambers of the first and second rotors and configured to identify the attribute of the assay fluid, wherein the assay fluids flow: (i) bi-directionally into and out of the assay chambers of one of the first and second rotors by displacement of the syringe plunger, (ii) from the first to the second rotors through a transfer channel formed in each of the radial walls and disposed between the first and second rotors, and (iii) into the auxiliary processing device and reaction chamber from the assay chambers of one of the second rotors to identify the requisite attribute of the assay fluid, wherein the transfer channel is configured to extend along a transfer channel axis, wherein the assay fluids flow through the transfer channel when the port axis aligns with the transfer channel axis.

2. The disposable cartridge of claim 1, wherein the transfer channel comprises a shape configured to facilitate the assay fluid flow between the first rotor and the second rotor.

3. The disposable cartridge of claim 1, wherein at least one of the ports of the first rotor is aligned with at least one of the ports of the second rotor along an axis which is substantially orthogonal to the axis of the syringe plunger.

4. The disposable cartridge of claim 1, wherein the first and second rotors are juxtaposed and a rotational axis of the first rotor is parallel to a rotational axis of the second rotor.

5. The disposable cartridge of claim 1, wherein the first and second rotors are tandem such that an axis of the syringe plunger intersects both rotors.

6. The disposable cartridge of claim 1 wherein the first and second rotors arc back-to-back such that a barrel port of a first syringe barrel injects an assay fluid into a first rotor and a barrel port of a second syringe barrel aspirates assay fluid from the second rotor.

7. The disposable cartridge of claim 5, wherein the axis of the syringe plunger defines an acute angle relative to a plane defined by the rotational axis of the first rotor and the rotational axis of the second rotors.

8. The disposable cartridge of claim 1, wherein the syringe barrel extends along a syringe barrel axis that is parallel to the transfer channel axis.

9. The disposable cartridge of claim 1, wherein each of the rotors comprises a bottom panel, wherein the plurality of assay chambers are molded along one side of the bottom panel.

10. The disposable cartridge of claim 9, wherein at least one channel is molded on an opposing underside of the bottom panel.

* * * * *